United States Patent [19]

Sesin

[11] Patent Number: 4,845,086

[45] Date of Patent: Jul. 4, 1989

[54] ANTIFUNGAL AGENT

[75] Inventor: David F. Sesin, Westfield, N.J.

[73] Assignee: Merck & Co., Inc., Rahway, N.J.

[21] Appl. No.: 230,284

[22] Filed: Aug. 9, 1988

[51] Int. Cl.$^4$ .................. A61K 31/395; C07D 273/08
[52] U.S. Cl. ..................................... 514/183; 540/454
[58] Field of Search ........................ 540/454; 514/183

[56] References Cited

U.S. PATENT DOCUMENTS 4,341,533  2/1983  Akimoto et al. .................... 540/461

OTHER PUBLICATIONS

Kupchan, S. M. et al., J. Am. Chem. Soc. 94:4, 1354 (1972).

Primary Examiner—Robert T. Bond
Attorney, Agent, or Firm—Alice O. Robertson; Michael C. Sudol

[57] ABSTRACT

A novel semi-synthetic compound, 10-[(3-chloro-4-methyoxyphenyl)methyl]-16-(2,3-dihydroxy-1-methyl-3-phenylpropyl)-6-methyl-3-(2-methylpropyl)-1,4-dioxa-8,11-diazacyclohexadec-13-ene-2,5,9,12-tetrone which has potential as a treating agent for mycotic infections is described.

3 Claims, No Drawings

ANTIFUNGAL AGENT

DESCRIPTION OF THE INVENTION

The present invention is directed to a new semi-synthetic compound represented by the formula:

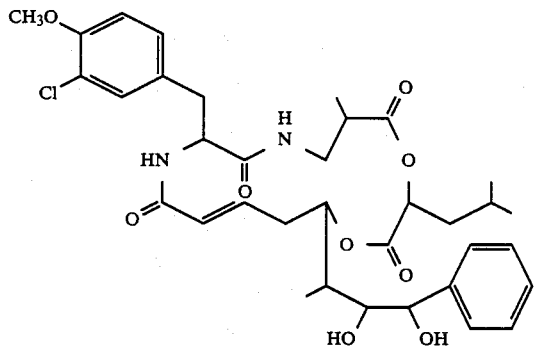

The compound also may be identified by the chemical name, 10-[(3-chloro-4-methoxyphenyl)methyl]-16-(2,3-dihydroxy-1-methyl-3-phenylpropyl)-6-methyl-3-(2-methylpropyl)-1,4-dioxa-8,11-diazacyclohexadec-13-ene-2,5,9,12-tetrone. For convenience, the compound hereinafter shall be referred to as Compound I.

Compound I has a molecular weight of 672, is of high solubility in organic solvents and adaptable to be employed in solution. It is also adaptable to be employed in aqueous dispersions.

Compound I may be produced by the oxidation of the corresponding olefin compound (Compound X) represented by the formula

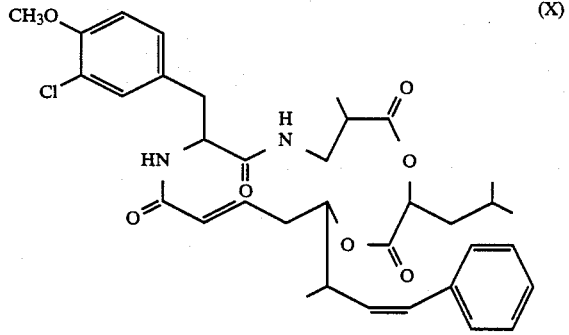

with glycol producing oxidizing agent such as osmium tetroxide.

Compound X may be produced by the deoxygenation of a natural product epoxide as hereinafter described and more fully disclosed in concurrently filed copending application Ser. No. 230-283 of David F. Sesin.

Osmium tetroxide is a well known reagent available commercially. It may also be prepared as directed in Fieser and Fieser "Reagents for Organic Synthesis" pp 759-764, John Wiley & Sons, Inc., New York and references cited therein. It is employed in this reaction in aqueous solution.

The exact amount of the oxidizing agent is not critical but generally a catalytic amount is used.

The reaction is carried out in methylene chloride and at ambient temperature.

The reaction is preferably monitored for the disappearance of Compound X by reverse phase analytical high performance liquid chromatography (HPLC column such as Zorbax from DuPont; of siliceous microparticulate porous particles; 4.6 mm×25 cm), using 50/50 acetonitrile/water as eluant.

In carrying out the reaction, a solution of osmium tetroxide and morpholine-N-oxide in methylene chloride is added to a solution of Compound X in methylene chloride and the mixture stirred at ambient temperature until HPLC analysis shows that the starting material has been consumed. The product (Compound I) may then be recovered from the reaction mixture by extracting with water, drying, concentrating the dried organic extract in vacuo and then chromatographing on a reverse phase column using 50/50 acetonitrile water as eluant.

Compound I is adapted to be employed for the control of fungal organisms, particularly the same organisms that are controlled by Compound Y such as Cryptococcus species among the yeast organisms and various filamentous fungi. Filamentous fungi include Aspergillus species, Penicillium species, Phoma species, *Alternaria solani, Cochliobolus miyabeanus, Botrytis allii, Ceratocystis ulmi, Fusarium oxysporum* and the like.

The antifungal properties are most effectively utilized when Compound I is formulated into antifungal treating compositions with a biologically inert carrier which in cases of use in pharmaceutical applications should also be pharmaceutically acceptable.

The novel compositions are formulated according to conventional compounding techniques with a biologically inert carrier, generally with the aid of a surface active dispersing agent. The compositions may contain 5 percent or more by weight of the active compound and, if a concentrate composition, may contain 15 percent or more. In preparing the composition, Compound I is intimately admixed with an appropriate carrier.

Suitable carriers include liquids such as water, glycol, oil, alcohols and the like which may include buffering agents, sodium chloride, dextrose and various suspending, stabilizing, solubilizing or dispersing agents. Solid carriers include starches, sugars, kaolin, ethyl cellulose, calcium carbonate, sodium carbonate, calcium phosphate, talc, lactose, and for tablets, lubricants such as calcium or magnesium stearate, binders, disintegrating agents and the like.

Compound I may also be formulated in creams and ointments such as white petrolatum, anhydrous lanolin, cetyl alcohol, cold cream, glyceryl monostearate, rose water and the like.

The antifungal compositions may be employed by applying to the area where fungal control is desired in such amounts as necessary to effect the desired control.

The following example illustrates the invention but is not to be construed as limiting.

EXAMPLE 100 microliters of a solution of 7.5 milligrams of osmium tetroxide in 5 milliliters of methylene chloride is added to a solution of 100 milligrams of Compound X and 20 milligrams of morpholine N-oxide in 10 milliliters of methylene chloride and the resulting mixture maintained at ambient temperature while the progress of the reaction as indicated by the disappearance of the starting material is monitored by reverse phase analytical HPLC (Zorbax 4.6 mm×25 cm) using 50/50 acetonitrile/water as eluting agent. After completion of the reaction, the reaction mixture is extracted with three 10 milliliter portions of water to remove morpholine. The organic solution is dried over anhydrous sodium sulfate, the volatiles removed under reduced pressure and the residue chromatographed on a reverse phase column (Zorbax 21.2 mm×25 cm) and eluted with 50/50 acetonitrile/water to obtain Compound I.

Starting Material

The starting material for the synthesis of Compound I is a semi-synthetic material, Compound X, which may be obtained by treating a natural product Compound Y

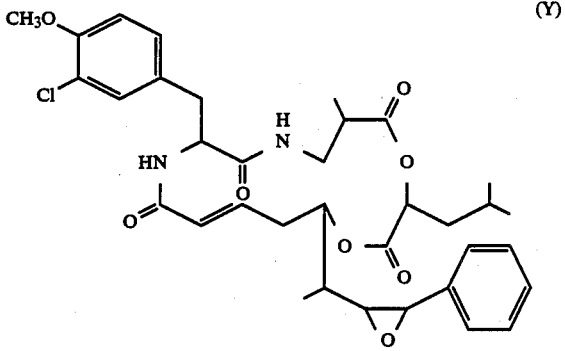

(Y)

with a deoxygenating agent such as diphosphorus tetraiodide or zinc-copper couple.

In a representative preparation of Compound X, Compound Y, is stirred together with zinc-copper couple in ethanol and the stirring continued under reflux until the reaction is complete as determined by the disappearance of Compound Y on HPLC assay. Compound X is recovered from the reaction mixture by first filtering to remove the metal oxides, vaporizing the volatiles under reduced pressure, then chromatographing the residue on a reverse phase HPLC column using 70/30 acetonitrile/water as eluant as more fully described in the aforementioned concurrently filed co-pending application of David F. Sesin.

Compound Y may be obtained by the cultivation of a cyanobacteria (Nostoc sp.) ATCC 53789 and isolating it from either a methanol extract of the cells or from the filtered (or supernatant) broth.

The cultivation may be carried out by inoculating a tube of Nostoc sp. culture ATCC 53789 in BG-13 medium and the inoculated culture incubated at 25° C. under a continuously replenished atmosphere of 5 percent (v/v) carbon dioxide in air and under continuous illumination at 5000 lux. At the end of this period, the cells are transferred to a larger (2-10 fold) volume of medium and the medium similarly cultivated under an atmosphere of 5 percent carbon dioxide in air and under continuous illumination at 5000 lux for 12-20 days to obtain Compound Y. The latter may be extracted from the cells with methanol or may be found in the fermentation broth and extracted with ethyl acetate. Compound Y may be recovered from the methanol extract by partitioning with methylene chloride and vaporizing the volatiles or from the ethyl acetate extract of the broth by vaporizing the volatiles and thereafter chromatographing the residue to purify the residue employing 75/25 methanol/water as eluant.

BG-13 medium is of the following composition in grams per liter: $NaNO_3$, 1.5-3.0; $NaHCO_3$, 1.7; $K_2HPO_4$, 0.031-0.34; sulfate as $MgSO_4.7H_2O$, 0.075 or $Na_2SO_4$, 0.14; $CaCl_2.H_2O$, 0.036; citric acid, 0.006; ferric ammonium citrate, 0.006; EDTA ($Na_2Mg$ salt), 0.001; $Na_2CO_3$, 0.02; trace element mix, 1 ml; and distilled water to 1000 ml wherein the trace element mix prepared in 0.1 N HCl, is of the following contents in grams per liter: $H_3BO_3$, 2.86; $MnCl_2.4H_2O$, 1.81; $ZnSO_4.7H_2O$, 0.222; $Na_2MoO_4.2H_2O$, 0.390; $CuSO_4.5H_2O$, 0.079; $CoCl_2.6H_2O$, 0.040; and wherein the pH of the solution is 7.6.

The production of Compound Y from Nostoc sp. is more fully described in copending application Ser. No. 17797 of Hirsch et al.

What is claimed is:
1. A compound of the formula:

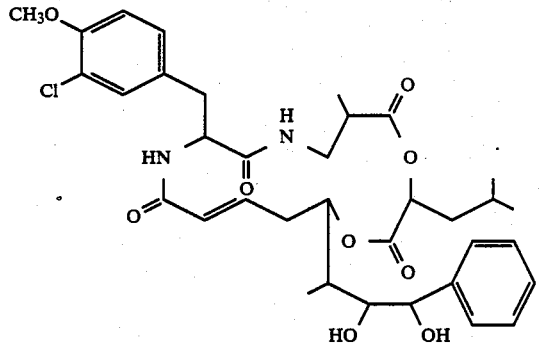

2. 10-[(3-Chloro-4-methoxyphenyl)methyl]-16-(2,3-dihydroxy-1-methyl-3-phenylpropyl)-6-methyl-3-(2-methylpropyl)-1,4-dioxa-8,11-diazacyclohexadec-13-ene-2,5,9,12-tetrone.

3. An antifungal composition comprising from about 5 to about 15 percent of the compound of claim 1 in admixture with a pharmaceutically acceptable carrier.

* * * * *